United States Patent [19]

Musikant et al.

[11] Patent Number: 5,413,480
[45] Date of Patent: May 9, 1995

[54] OVERDENTURE ATTACHMENT SYSTEM

[75] Inventors: Barry L. Musikant; Allan S. Deutsch, both of New York; Brett I. Cohen, Nanuet, all of N.Y.

[73] Assignee: Essential Dental Systems, Inc., South Hackensack, N.J.

[21] Appl. No.: 118,509

[22] Filed: Sep. 8, 1993

[51] Int. Cl.⁶ .................... A61C 8/00; A61C 13/12; A61C 13/225
[52] U.S. Cl. .................... 433/173; 433/181; 433/182
[58] Field of Search ............... 433/167, 172, 169, 173, 433/174, 177, 181, 182, 183, 193, 194, 195, 220, 221

[56] References Cited

U.S. PATENT DOCUMENTS

| | | | |
|---|---|---|---|
| 866,304 | 9/1907 | Roach | 433/183 X |
| 1,279,805 | 9/1918 | Whitaker | 433/194 |
| 3,082,525 | 3/1963 | Christensen | 433/174 |
| 3,328,879 | 7/1967 | Bax | 433/177 X |
| 3,787,975 | 1/1974 | Zuest | 433/182 |
| 4,204,321 | 5/1980 | Scott | 433/177 |
| 4,540,367 | 9/1985 | Sulc | 433/181 |
| 4,547,156 | 10/1985 | Hader | 433/172 |
| 4,681,542 | 7/1987 | Baum | 433/172 |
| 4,756,689 | 7/1988 | Lundgren et al. | 433/173 |
| 4,850,870 | 7/1989 | Lazzara et al. | 433/174 |
| 4,973,249 | 11/1990 | Silvio et al. | 433/182 |
| 4,976,739 | 12/1990 | Duthie, Jr. | 433/174 X |
| 5,006,069 | 4/1991 | Lazzara et al. | 433/141 X |
| 5,030,094 | 7/1991 | Nardi et al. | 433/169 |
| 5,049,072 | 9/1991 | Lueschen | 433/177 X |
| 5,071,351 | 12/1991 | Green, Jr. et al. | 433/173 |
| 5,092,770 | 3/1992 | Zakula | 433/172 |
| 5,106,300 | 4/1992 | Voitik | 433/173 |
| 5,108,288 | 4/1992 | Perry | 433/174 X |
| 5,116,225 | 5/1992 | Riera | 433/173 |
| 5,145,371 | 9/1992 | Jorneus | 433/173 |

OTHER PUBLICATIONS

Advertisement entitled "Now Replace Zest Males in 30 Seconds Flat", Found on p. 466 of Sep., 1983, *Dental Products Report.*

*Primary Examiner*—Nicholas D. Lucchesi
*Attorney, Agent, or Firm*—Gottlieb, Rackman & Reisman

[57] ABSTRACT

An overdenture attachment system for selectively attaching a denture element to a post in a tooth or a root canal is provided. The system includes a keeper element which is designed to be permanently affixed to the denture element and a cap element that is designed for attachment to the post of the tooth or root canal and which is coupled to or received by the keeper element. In the preferred embodiment, the keeper element is formed with a flange portion in which the insert element is selectively received. The interior of the flange portion of the keeper element is threaded and the exterior of the cap element is correspondingly threaded in order to enable threaded engagement of the cap element inside the keeper element.

14 Claims, 2 Drawing Sheets

OVERDENTURE ATTACHMENT SYSTEM

BACKGROUND

This invention relates to an overdenture attachment system, and more particularly to a system for selectively attaching a denture element to a post in a tooth or root canal.

Traditionally, pre-fabricated overdenture attachment systems consisted of a pre-fabricated post that was cemented into a tooth or root canal and a plastic or metal fixture element which is placed into the acrylic denture. The fixture element is used for attaching the post to the denture element. Since most prior art fixture elements that are placed into the denture are made of plastic, after prolonged use, these fixture elements wear out. As a result, retention of the denture to the post in the root canal or tooth is greatly reduced over time.

Therefore, when these fixture elements or overdenture caps finally wear out, the dentist or dental practitioner has to replace the fixture element by typically taking a dental burr and cutting the element from the denture. Not only is this time consuming, but there is a significant risk of damage to the denture element. Notwithstanding, once the dental practitioner has removed the fixture element, a new fixture element or cap is placed on the post head and cemented into the denture element with a cold cured acrylic or light cured acrylic.

Accordingly, it would be desirable to provide an overdenture attachment system which would overcome these disadvantages, and which may be easily repaired and/or replaced as needed.

SUMMARY OF THE INVENTION

Generally speaking, in accordance with the invention, an overdenture attachment system for selectively attaching a denture element to a post in a tooth or a root canal is provided. The system includes a keeper element which is designed to be permanently affixed to the denture element and a cap element that is designed for attachment to the post of the tooth or root canal and which is coupled to or received by the keeper element. In the preferred embodiment, the keeper element is formed with a flange portion in which the insert element is selectively received. The interior of the flange portion of the keeper element is threaded and the exterior of the cap element is correspondingly threaded in order to enable threaded engagement of the cap element inside the keeper element.

In accordance with the invention, when the cap element is threaded into the keeper element, the cap element is permanently seated and locked into place. This is achieved by using a specially designed tool or handle that is used for threading the cap element inside the keeper element, or for removing it therefrom.

In using the overdenture system of the invention, the keeper element is first permanently affixed to the denture element. Then the cap element is threaded into the keeper element until it locks into place. When the cap element wears out due to exposure in the oral environment, the tool or handle is used to remove the cap element and a new cap element is threaded into the keeper element by the dental practitioner.

Accordingly, it is an object of the invention to provide an improved overdenture attachment system.

Another object of the invention is to provide an overdenture attachment system which is easily repaired.

A further object of the invention is to provide an overdenture attachment system which includes one element that is permanently affixed to the denture.

Still another object of the invention is to provide an overdenture attachment system that includes a replaceable second element.

Still other objects and advantages of the invention will in part be obvious and will in part be apparent from the following description.

The invention comprises the several components and the relation of one or more such components with respect to each of the others.

BRIEF DESCRIPTION OF THE DRAWINGS

For a fuller understanding of the invention, reference is made to the following description taken in connection with the accompanying drawings, in which.

DETAILED DESCRIPTION OF THE PREFERRED EMBODIMENT

Referring first to FIGS. 2 and 4–6, a prefabricated post 18 is shown cemented into a tooth 22 of the patient. Post 18 includes a ball 20 sitting on the top thereof that is used in connecting post 18 to a denture element, as described in greater detail below. Post 18 has grooves or threads (not shown) as is well known in the art in order to facilitate retention inside tooth 22 with the use of conventional cements.

Figure 1:
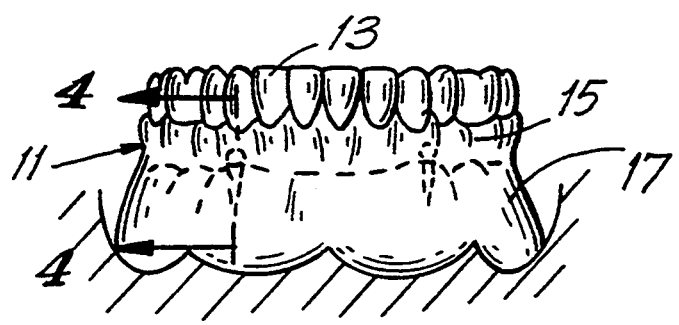
FIG. 1 is a front elevational view showing a lower denture element affixed to the lower gum of a patient using the inventive attachment system.
Figure 2:
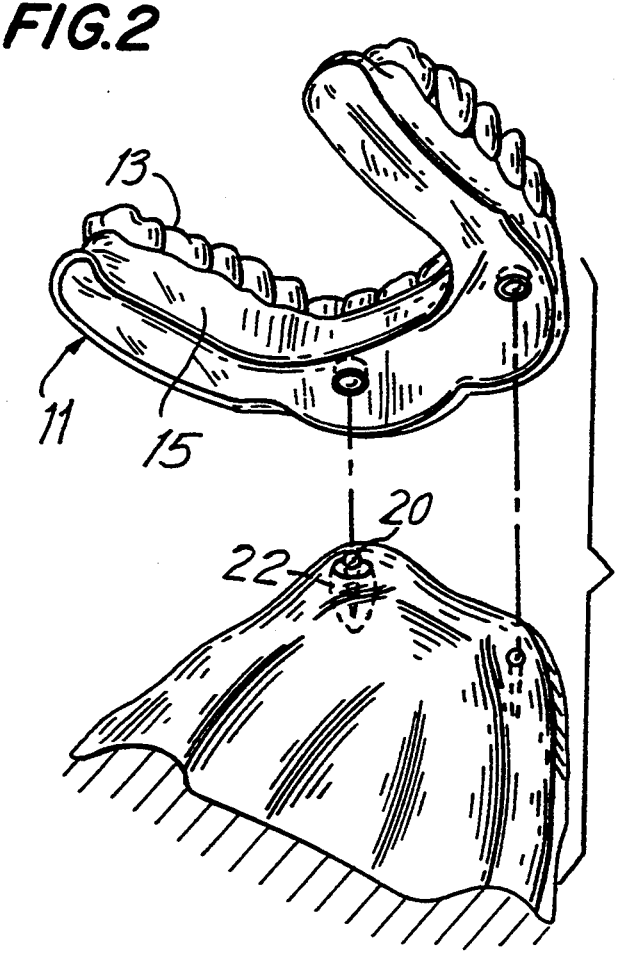
FIG. 2 is an exploded perspective view showing the denture element of FIG. 1 separated from the lower gum of a patient.

Referring now to FIGS. 1 and 2, an overdenture element generally indicated 11 is shown and includes a series of teeth 13 and a connecting bridge 15 as is well known in the art. In use, denture element 11 is seated in the lower gum of the patient by means of post 18 and ball 20. In prior art systems, a permanent fixture element was placed in denture element 11 used for reception of post 18 with upper ball 20. However, as described in the background portion of this application, this system is less than satisfactory.

Figure 3:
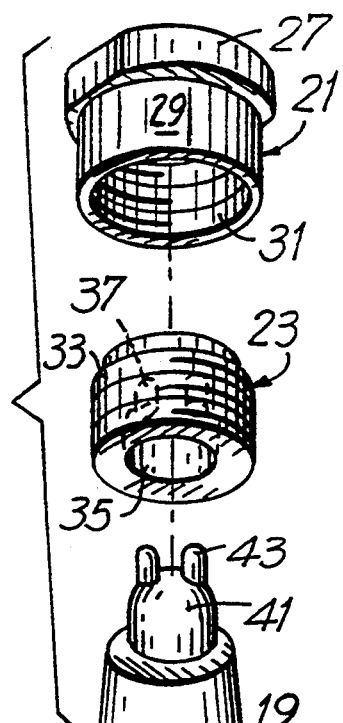
FIG. 3 is an exploded perspective view of the overdenture attachment system of the invention, including the cap element and the keeper element.

Turning now to FIG. 3, the overdenture attachment system of the invention is shown and is generally indicated at 19. Attachment system 19 comprises a keeper element 21 that is adapted to be permanently affixed to denture element 11, a cap element 23 which is designed for selective connection to post 18 received in tooth 22 of the patient and which may be selectively coupled to keeper element 21, and a tool 25 that is used for selectively removing cap element 23 from keeper element 21.

Keeper element 21 comprises a head 27 and an annular flange 29. Annular flange 29 includes a threaded interior 31 that is used for selectively receiving cap element 23. As shown in FIG. 3, cap element 23 comprises an annular threaded exterior having a threaded configuration which corresponds with threaded interior 31 of keeper element 21. Cap element 23 also includes a socket 35 that is designed for receiving ball 20 of post 18. Socket 35 includes a pair of upwardly extending slots 37 that are designed for mating engagement with the prongs of tool 25, as described in more detail hereinafter.

Tool 25 is also shown in FIG. 3 and includes an extending handle portion 39 that is used by the operator for gripping tool 25 during operation thereof. Tool 25 also includes a head 41 located at one end thereof from which a pair of prongs 43 extend. Prongs 43 are sized to fit into slots 37 formed in socket 35 of cap element 23 in order to use tool 25 for threading and unthreading cap element 23 into and from keeper element 21.

Figure 4:
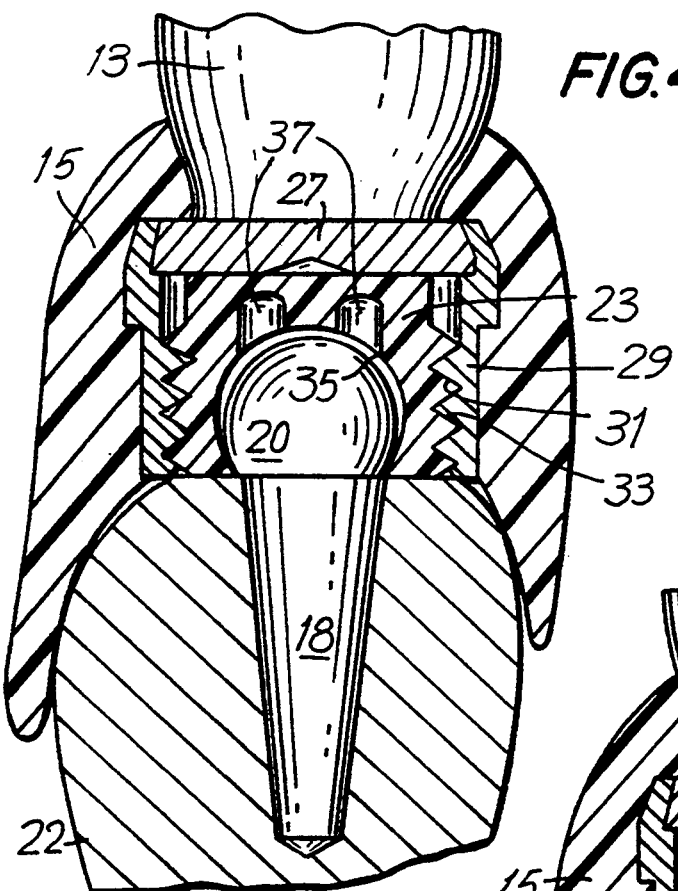
FIG. 4 is a cross-sectional view taken along line 4—4 of FIG. 1.
Figure 5:
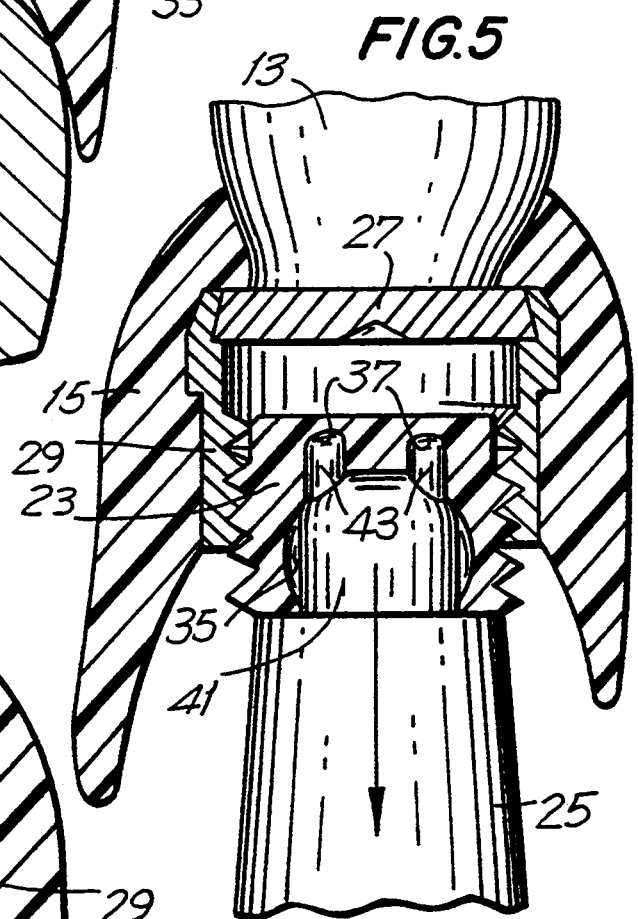
FIG. 5 is a cross-sectional view that is similar to FIG. 4 and shows removal of the cap element from the keeper element.
Figure 6:
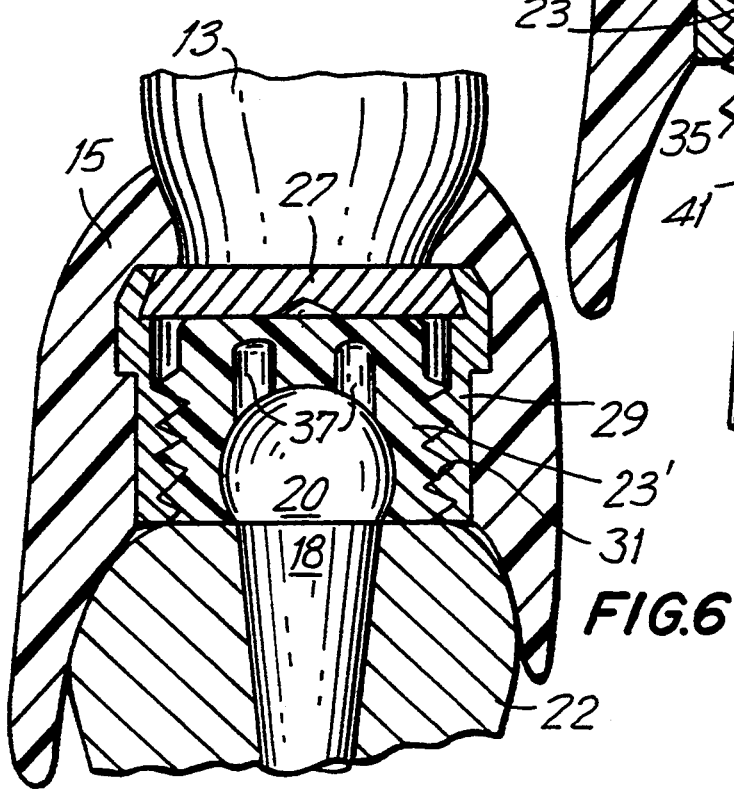
FIG. 6 is a cross-sectional view that is similar to FIGS. 4 and 5 and shows the insertion of a new cap element into the keeper element.

Referring now to FIGS. 4–6, operation of overdenture attachment system 19 is illustrated. In FIG. 4, cap element 23 has been threaded into keeper element 21 and is therefore permanently locked into place. This has been achieved by using tool 25 as discussed below. Frequently, cap element 23 wears out, i.e., from excessive exposure in the oral environment. As shown in FIG. 5, after unseating denture element 11 from the patient's lower gum, tool 25 is used to remove cap element 23 from keeper element 21, which is permanently affixed to denture element 11. By inserting prongs 43 of tool 25 into corresponding slots 37 of cap element 23, the operator is able to unscrew or threadingly disengage cap element 23 from keeper element 21.

FIG. 6 describes the insertion of a new cap element 23' into permanently affixed keeper element 21. This is achieved by once again using prongs 43 of tool 25 and inserting the prongs into the slot of new cap element 23'. Thereafter, new cap element 23' is threadingly rotated inside flange 29 of keeper element 21.

Once the new cap element has been attached to keeper element 21, denture element 11 may once again be seated in the lower gum of the patient. Ball 20 of post 18 is force fitted into socket 35 of new cap element 23' retained in denture element 11, as is well known in the art and shown in FIG. 6.

Although the inventive denture attachment system is shown in the drawings for use in attaching a denture element to a post retained in a tooth, it may also be used for attaching a denture element to a post retained in a root canal.

Although the inventive denture attachment system is shown in the drawings for use in attaching a denture element to a post retained in a tooth, it may also be used for attaching a denture element to an abutment or other fixture fixed in an implant that is formed in the jaw bone.

It will thus be seen that the objects set forth above, among those made apparent in the preceding description are efficiently attained and, since certain changes may be made in the described system and in the construction set forth above without departing from the spirit and scope of the invention, it is intended that all matter contained in the above description and found in the accompanying drawings shall be interpreted as illustrative and not in a limiting sense.

We claim:

1. An overdenture attachment system comprising:
    a keeper element permanently affixed to a denture element and including a flange with a threaded interior;
    a dental implant adapted to be fixed in and extend from a tooth, root canal or oral bone; and
    a cap element releasably connectible to said keeper element by means of a threaded exterior and having socket means for selective releasible coupling with said extending implant including means for enabling selective rotation of said cap element with respect to said keeper element;
    wherein said cap element is adapted to be selectively and releasibly threaded into and unthreaded from said flange of said keeper element by operating on said rotation enabling means once said cap element is uncoupled from said extending implant.

2. The system of claim 1, wherein said socket is sized for receiving said extending implant in a force fit arrangement.

3. The system of claim 1, wherein said keeper element is made of metal.

4. The system of claim 1, wherein said cap element is made of plastic.

5. The system of claim 1, further including a tool for selectively threading and unthreading said cap element into and from said keeper element flange.

6. The system of claim 5, wherein said tool element is operational on said rotation enabling means.

7. The system of claim 6, wherein said rotation enabling means comprises at least one slot for selective engagement with said tool element.

8. An overdenture attachment system comprising:
    a keeper element permanently affixed to a denture element and including a flange;
    a dental implant adapted to be fixed in and extend from a tooth, root canal or oral bone;
    a cap element releasibly connectible to said keeper element and comprising an insert for releasibly threaded engagement in said keeper element flange,
    said cap element having socket means for selective releasible coupling with said implant, the socket means including means for enabling selective removal of said cap element from said keeper element once said cap element is uncoupled from said enabling means.

9. The system of claim 8, wherein said keeper element is metal, said dental implant is metal and said cap element is plastic.

10. The system of claim 8, wherein said removal means comprises means for enabling selective rotation of said cap element.

11. An overdenture attachment system comprising:
    a keeper element permanently affixed to a denture element having a flange with an interior;
    a dental implant adapted to be fixed in and extend from a tooth, root canal or oral bone;
    a cap element releasibly connectible to and disconnectible from said keeper element and comprising an insert having an exterior for selective reception within the interior of said flange, the cap element having socket means for selective releasible coupling with said extending portion of said implant, the socket means including means for enabling selective removal of said cap element from said keeper element once said cap element is uncoupled from said extending implant.

12. The system of claim 11, wherein said keeper element is metal and said dental implant is metal.

13. The system of claim 11, wherein said removal means comprises means for enabling selective rotation of said cap element.

14. The system of claim 13, further including a tool element for operating on said removal enabling means for selectively connecting and disconnecting said cap element to and from said keeper element.

* * * * *